United States Patent [19]

Siepmann et al.

[11] Patent Number: 4,898,829
[45] Date of Patent: Feb. 6, 1990

[54] APPARATUS FOR THE DETECTION OF BIODEGRADABLE AND TOXIC SUBSTANCES IN AQUEOUS SOLUTIONS

[76] Inventors: Friedrich W. Siepmann, Frankfurter Str. 10, D-6100 Darmstadt; Michael Teutscher, Heinrichstr. 5, D-6111 Otzberg 4, both of Fed. Rep. of Germany

[21] Appl. No.: 132,267

[22] Filed: Dec. 14, 1987

Related U.S. Application Data

[60] Division of Ser. No. 693,836, Jan. 23, 1985, Pat. No. 4,748,127, which is a continuation of Ser. No. 387,837, filed as PCT EP81/00162 on Oct. 10, 1981, abandoned.

[30] Foreign Application Priority Data

Oct. 10, 1980 [DE] Fed. Rep. of Germany ....... 3038305
Oct. 10, 1981 [WO] PCT Int'l Appl. ... PCT/EP81/00162

[51] Int. Cl.$^4$ .................... C12M 1/36; C12M 1/34
[52] U.S. Cl. .................... 435/289; 422/79; 422/111; 435/3; 435/29; 435/32; 435/291; 436/50; 436/52; 436/55; 436/62; 436/138; 436/179
[58] Field of Search .............. 422/79, 111; 436/34, 436/50, 52, 55, 62, 138, 179; 435/3, 29, 32, 289, 291, 807

[56] References Cited

U.S. PATENT DOCUMENTS 3,684,702 8/1972 Hartmann .
3,731,522 5/1973 Mikesell .
3,766,010 10/1973 Ikeda et al. .
4,073,692 2/1978 Ciaccio et al. .
4,162,195 7/1979 Solyom et al. .

FOREIGN PATENT DOCUMENTS 2415771 10/1975 Fed. Rep. of Germany .

Primary Examiner—Robert J. Hill, Jr.
Attorney, Agent, or Firm—Andrus, Sceales, Starke & Sawall

[57] ABSTRACT

A process and apparatus for measuring the degree of pollution, the degradableness, and the level of toxicity of aqueous liquids, for example, effluent. A partial stream is withdrawn from the liquid undergoing examination and diluted with biologically neutral water. The diluted partial stream is oxygenated and continuously flows through a biological bath in a reaction vessel having a constant living mass. The dilution of the partial stream is regulated in such a manner through measurement of the oxygen content upstream and downstream of the reaction vessel, that with constant volume flow through the reaction vessel, the difference between the measurement values obtained remains essentially constant at a predetermined value, so that the amount of dilution serves for the indication of the level of pollution. Additional reaction vessels connected in parallel or in series with the first reaction vessel and having associated oxygen electrodes allows measurement of the toxicity and degradableness of the pollution.

42 Claims, 5 Drawing Sheets

APPARATUS FOR THE DETECTION OF BIODEGRADABLE AND TOXIC SUBSTANCES IN AQUEOUS SOLUTIONS

CROSS REFERENCE TO RELATED APPLICATION

This application is a divisional application of U.S. patent application Ser. No. 06/693,836, filed Jan. 23, 1985 and now U.S. Pat. No. 4,748,127. That application is, in turn, a continuation application of U.S. patent application 06/387,873, filed as PCT EP81/00162 on Oct. 10, 1981, and now abandoned.

BACKGROUND OF THE INVENTION

The invention relates to a process and apparatus for measuring the degree of pollution of aqueous liquids, for example effluents, through biodegradable components. In the process and apparatus of the invention, a partial stream is withdrawn from the liquid undergoing examination. The partial stream is oxygenated and continuously flows through a biological bath in a reaction vessel, after which its residual oxygen content is measured. In the technique of the present invention, the living mass of the bath is held at an essentially constant level.

The determination of the biological oxygen demand has heretofore generally been carried out with a standardized random sample process, in which the result is ascertained after five days (so-called BOD$_5$). The requirements therefor are established in the "German Standard Process H 4". Continuously working apparatuses are not heretofore known.

For the determination of the toxic effects in aqueous liquids, tests with fish or bacteria cultures are usually carried out. The results of the tests provide a positive or negative indication. From DE-OS No. 2,514,609, a process and device for the measurement of the acute toxicity of aqueous liquids is known. With this process and device, it is not possible to differentiate between degradable contamination decline and low toxicity levels in, for example, effluents as only a positive or negative indication is given.

SUMMARY OF THE INVENTION

The object of the present invention is to provide processes and apparatuses with which continuous measurement of biodegradable pollution can be carried out. Particularly the inhibition of microorganisms in the presence of toxically active substances in the aqueous liquids, in particular sewage or effluents, can be determined.

For the attainment of this object, the model of Michaelis and Menten confirmed in many experiments is utilized as a theoretical basis. The expression of the biochemical reaction speed in dependence on the nutrient supply is represented by the formula $$V = V_{max} \cdot \frac{L}{K_m + L} \quad (1)$$

wherein
V = reaction speed
$V_{max}$ = maximum reaction speed
L = nutrient supply (concentration)
$K_m$ = Michaelis constant For small nutrient supply, the Michaelis equation is in the first approximation a simplified form $$V = V_{max} \cdot \frac{L}{K_m} \quad (2)$$

From the practical standpoint, the expression of the equation (2) means that, with low substrate or nutrient supply concentrations, the reaction speed is proportional to nutrient supply concentration; that is, a nutrient supply increase calls for a linear oxygen consumption increase in this region. It may be assumed, then, that if the oxygen content does not sink under 15% of its saturation value, it does not give rise to an "initiating reaction".

The Michaelis equation is valid in a significant sense only for a constant enzyme amount with variable substrate concentration and with unimpeded diffusion of the nutrient material to the enzyme. These conditions can be insured, as tests have shown, through moving, hollow bodies as growing substrate surfaces for the organisms, constant magnitude circulating speed in the reaction vessel and thus similar organism growth and cleansing rates.

Emanating from the foregoing, the solution of the present invention comprises a modification of the previously mentioned known process of DE-OS No. 2,514,609, that is characterized in that the partial stream is diluted with biologically neutral water. The dilution of the partial stream is regulated in such a way, through measurement of the oxygen content ahead of the reaction vessel and comparison with the measurement result of the residual oxygen content, that with constant volume flow through the reaction vessel the difference of the measured values is essentially held constant at a predetermined value. The amount of dilution thus serves as the indication of the level of pollution.

The oxygen content of the partial stream of the fluid to be examined is consequently measured at the inlet and the outlet of the reaction vessel, in which the growth surfaces for the microorganisms are located. The difference in oxygen content is held constant in a small deviation range so that with oxygen differences that become smaller, the added portion of the dilution water is reduced, while with differences that grow greater it is increased. Thus a constant substrate or nutrient supply and a constant oxygen consumption of the microorganisms in the reaction vessel is assured. With unchanging growth surfaces in the reaction vessel, a constant organism amount is provided through continuous scouring and washing off. Particularly useful are movable, hollow bodies that offer growth surfaces protected against abrasion.

According to the invention, the concentration "$L_k$" of nutrient supplied to the reaction vessel should be selected from the region of approximately linear slope of the curve relating the reaction speed of the living mass to the nutrient supply. This is inter alia to be expected if the reaction speed is lower than half the maximum reaction speed ($V_k < V_{max}/2$). In this region both a very spontaneous reaction of the living mass to concentration fluctuations can be expected as well as also the basis laid for a linear slope.

With the pH variations to be expected in the fluid undergoing examination, inhibiting actions on the microorganisms can be prevented through a corresponding supply metering of a biologically neutral buffer solution.

Through the application of a light pressure in the apparatus, a better oxygen solubility can be achieved and the development of gas bubbles in the apparatus parts can be prevented.

With the constant microbiological activity contained in the reaction vessel according to the invention, an indication can be obtained, from the dilution ratio as well as from the measured $O_2$ difference and the temperature, of the biodegradable contaminants in the fluid undergoing examination, that can be expressed directly as a $BOD_5$ value through comparative measurements and calibration of the apparatus. Application fields of this BOD measuring process are, for example, the recording of the biodegradable pollutant load in clarifier apparatus and the control of such apparatus according to the actual oxygen demand.

With the presence of toxic components in the fluid undergoing examination, an inhibition of the microorganisms occurs, the amount of which depends on the concentration of the toxic material.

For the determination of the toxicity, in a refinement of the process according to the invention, a second partial stream is drawn out of the liquid undergoing examination and treated in a similar manner. However, the dilution level of the second partial stream is regulated lower by a constant factor (m) than that of the first partial stream and the difference of the measured values before and after the second reaction vessel is compared with the measured values from the first partial stream and indicated as the level of toxicity.

With parallel operation of two reaction vessels, in which the dilution in the first vessel is regulated according to the described process, a partial stream diluted less by the factor "m" is always supplied to the second vessel, so that in the second vessel the toxic substance always exists in the m-fold concentration. From a diminished oxygen consumption in the second vessel, then, conclusions as to the presence and the amount of a toxic activity can be drawn, if the dilution amount in the first vessel is so adjusted that the toxic component in the first vessel no longer acts in an inhibiting manner.

The toxicity measurement according to the invention thus concerns two parallel flowing BOD measurements with different dilution amounts. As the inhibiting action of the toxic substances increases over proportionally with increased concentration, this permits the toxicity level to be expressed as a ratio of the measured activity $BOD_a/BOD_b$ in both partial streams a,b relative to the dilution level in the first vessel.

The application field of the process includes for example, use as a warning system for biological apparatus parts in clarifiers of impending toxic effluent surges.

In a further configuration of the invention for the determination of the toxic effects of aqueous liquid in absolute values, a "biological standard" is initially cultured and maintained in the reaction vessels with a nutrient solution of known composition without any toxic influence. Then the hazardous aqueous liquid is supplied to the "biological standard" and the activity of the organisms recorded. For the organisms, recorded uninhibited respiration activity so-called null point values exist on the basis of previous measurements. With a so calibrated discontinuous measurement, absolute toxicity relative to a "biological standard" can thus be indicated.

The invention concerns itself further with an apparatus for measuring the biodegradable pollutants in aqueous liquids, in particular sewage and effluents, as well as for the measurement of the inhibiting action of toxic components on microorganisms.

The apparatus for carrying out the process has a aeration tank and a reaction vessel, through which the partial stream drawn off the aqueous liquid flows. An oxygen electrode is located in the discharge conduit of the reaction vessel. According to the invention, on the inlet side of the aeration tank, the supply conduit of the partial stream is brought together with a supply conduit for the dilution water. A flow regulating apparatus connected to a control lies in the supply conduit for the dilution water. An oxygen electrode also connected to the control is arranged in the conduit connecting the outlet of the aeration tank with the feed of the reaction vessel. The control contains a comparator and an adjustment signal generator for the flow regulating device. The flow regulating device can be expediently realized in such a manner that a metering pump is arranged in each of the supply conduit for the partial stream and the supply conduit for the dilution water.

The growing surfaces in the reaction vessel are formed out of freely movable bodies with growing surfaces protected against abrasion. The bodies and the container contents are preferably continuously intermixed through an agitation or circulating device. Ahead of the inlet conduit in the aerator, the liquid to be tested can run through a sieve and an agitator for thorough homogenization.

With the measured $O_2$ values, the ratio of the flow amounts of the liquid undergoing examination and of the dilution water is so controlled through a process controller that, with a constant flow stream in the reaction vessel, a constant $O_2$ difference appears and the output does not fall below a minimum value. The magnitude of the required adjustement is utilized for the indication of the level of pollution.

A second, similar reaction vessel, that is connected in series with the first reaction vessel and is equipped with oxygen electrodes connected ahead and behind it, can be used for the determination of the degradableness of the pollutant of the partial stream as well as, alternatively, for toxicity measurement.

In a refinement of the process according to the invention for the determination of toxicity through the series arrangement for BOD-measurement, the liquid undergoing examination is treated a second time in a similar manner. In the second treatment, however, the dilution level in the second reaction vessel is regulated greater by a constant factor (m) than that in the first reaction vessel and the difference of the measured values ahead and behind the second reaction vessel is compared with the measured values of the first reaction vessel and indicated as a toxicity level.

With the series arranged operation of two reaction vessels and with the dilution in the first vessel according to the described process, it can be so regulated through the oxygen electrodes of the subsequently connected vessel (17) that a partial stream more diluted by the factor "m" is always supplied to the scond vessel, so that in the second vessel a toxic substance always occurs in the m-fold smaller concentration. From a diminished oxygen consumption in the first vessel, then, conclusions can be drawn as to the presence and the level of a toxic action, if the dilution level in the subsequently connected vessel is so adjusted that the toxic component in that vessel acts in a non-inhibiting manner.

With the toxicity measurement according to the invention, there is also concerned two successively conducted BOD measurements with different dilution levels. As the inhibiting action of the toxic substance is over proportionally increased with increased concentration, the toxicity level can be expressed as a ratio of the activity measured in the two reaction vessels with respect to the dilution level in the second vessel.

If the microorganisms are persistently harmed through a strongly toxic action, the grown over suspended bodies can be removed from the reaction vessel and can be exchanged for a new batch with uncontaminated biological cultures.

BRIEF DESCRIPTION OF THE DRAWINGS

In the following, the invention is explained with the aid of the associated drawings. The drawings show FIG. 1 an apparatus for the measurement of BOD.

DETAILED DESCRIPTION OF THE INVENTION

Figure 1:
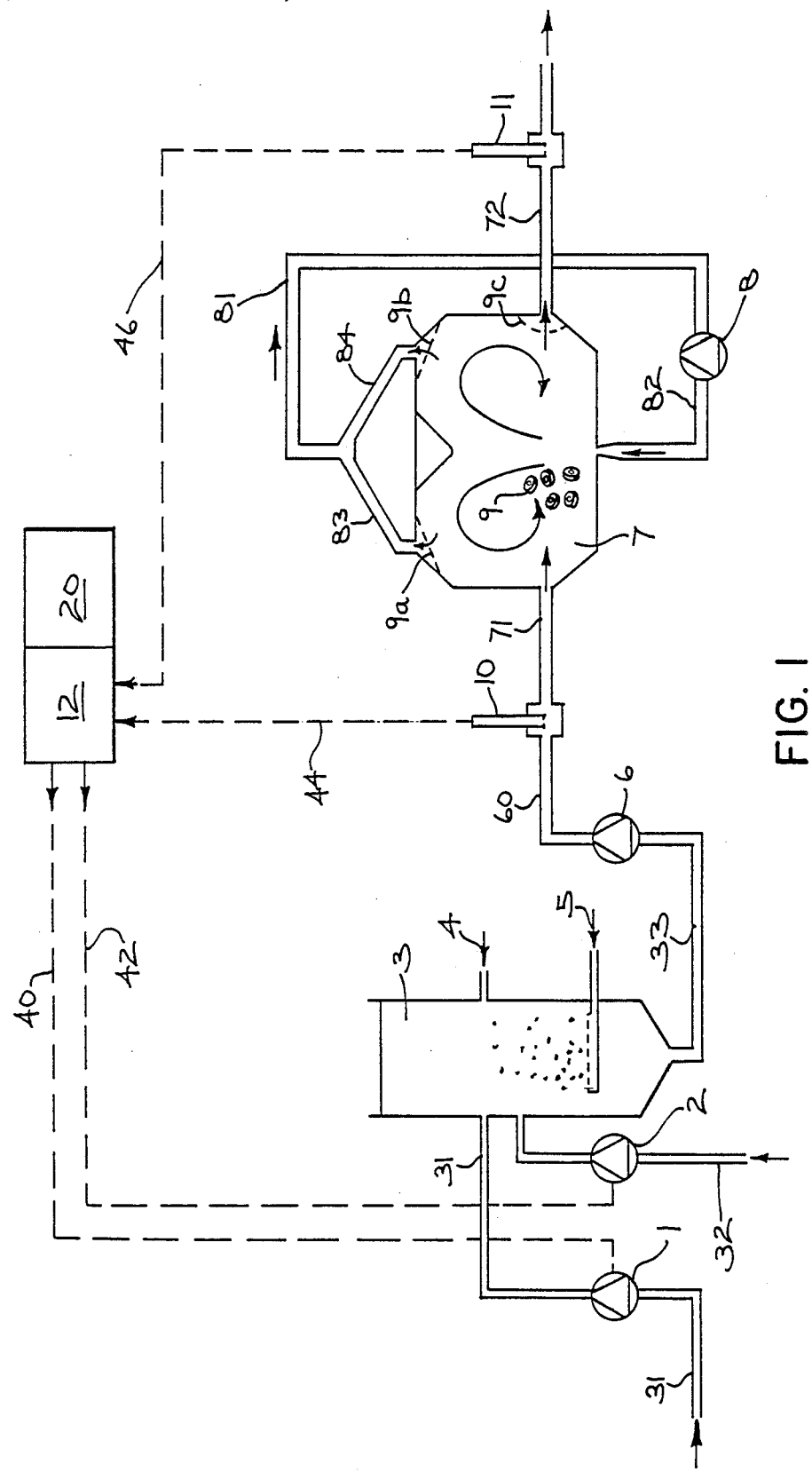

According to FIG. 1 the fluid to be examined in conduit 31 and the dilution water in conduit 32 are fed through the metering pump 1 and the metering pump 2, respectively, to the inlet side of an aeration tank 3, in which, a fluid for the pH-buffering is added to the mixture through a further supply conduit 4. Through entrainment of air or gaseous oxygen by means of a supply conduit 5, the fluid contained in the aeration tank 3 is enriched with oxygen. The fluid flow removed from the aeration tank 3 through outlet conduit 33 is supplied through a pump 6 to a reaction tank 7 in a constant stream through a supply conduit 71. In the conduit 60 connecting the supply conduit 71 with the pump 6 is connected a first oxygen electrode 10, which measures the oxygen content and the temperature of the flowing liquid and supplies the measured values to a control containing process controller 12.

The fluid stream entering the upwardly closed reaction vessel 7 through the conduit 71 leaves this vessel through a discharge conduit 72 arranged on the oppositely lying end of the reaction vessel 7 in which a further oxygen electrode 11 is arranged. The oxygen electrode 11 senses the temperature and the oxygen content of the discharge flow and conducts the measured values in the form of signals to the process controller 12. On the discharge side of the oxygen electrode 11 the discharge conduit 72 opens into a not disclosed waste tank.

The reaction tank 7 is connected in a return line 81, 82 through which the liquid contained in the reaction container 7 is continuously circulated. The return conduit 82, connected on the discharge side of the circulating pump 8, opens in the bottom of the reaction vessel 7 and the fluid out of the reaction vessel 7 enters recirculating conduit 81 connected through a plurality of branch conduits 82, 84 in the lid of the reaction vessel 7.

In the reaction vessel, a large number of suspended bodies 9 with growing surfaces for the microorganisms are contained, that through the recirculated liquid are in constant movement in the reaction vessel 7. Return screens 9a, 9b, 9c with a small mesh size with respect to the size of the suspended bodies 9 are arranged ahead of the discharge openings out of the reaction vessel in the conduits 83 and 84 as well as conduit 72. Alternative to the recycling circuit 81, 82, a not-disclosed agitator can be provided in the reaction vessel 7, driven either from the flow out of the supply conduit 71 or separately from the outside.

The control contains an indicating apparatus 20 controlled from process controller 12, that indicates or prints out the BOD value determined from the process controller 12. A control conductor 40 leads out of the process controller 12 to the metering pump 1 in the inlet conduit 31 for the aeration tank 3. A control conductor 42 leads out of the process controller 12 to a metering pump 2 in the supply conduit 32 for the dilution water. The control conductors 44, 46 between the first oxygen electrode 10 and the second oxygen electrode 11, respectively, and the process controller 12 convey the ascertained values from the oxygen electrodes to the process controller 12.

Figure 2:
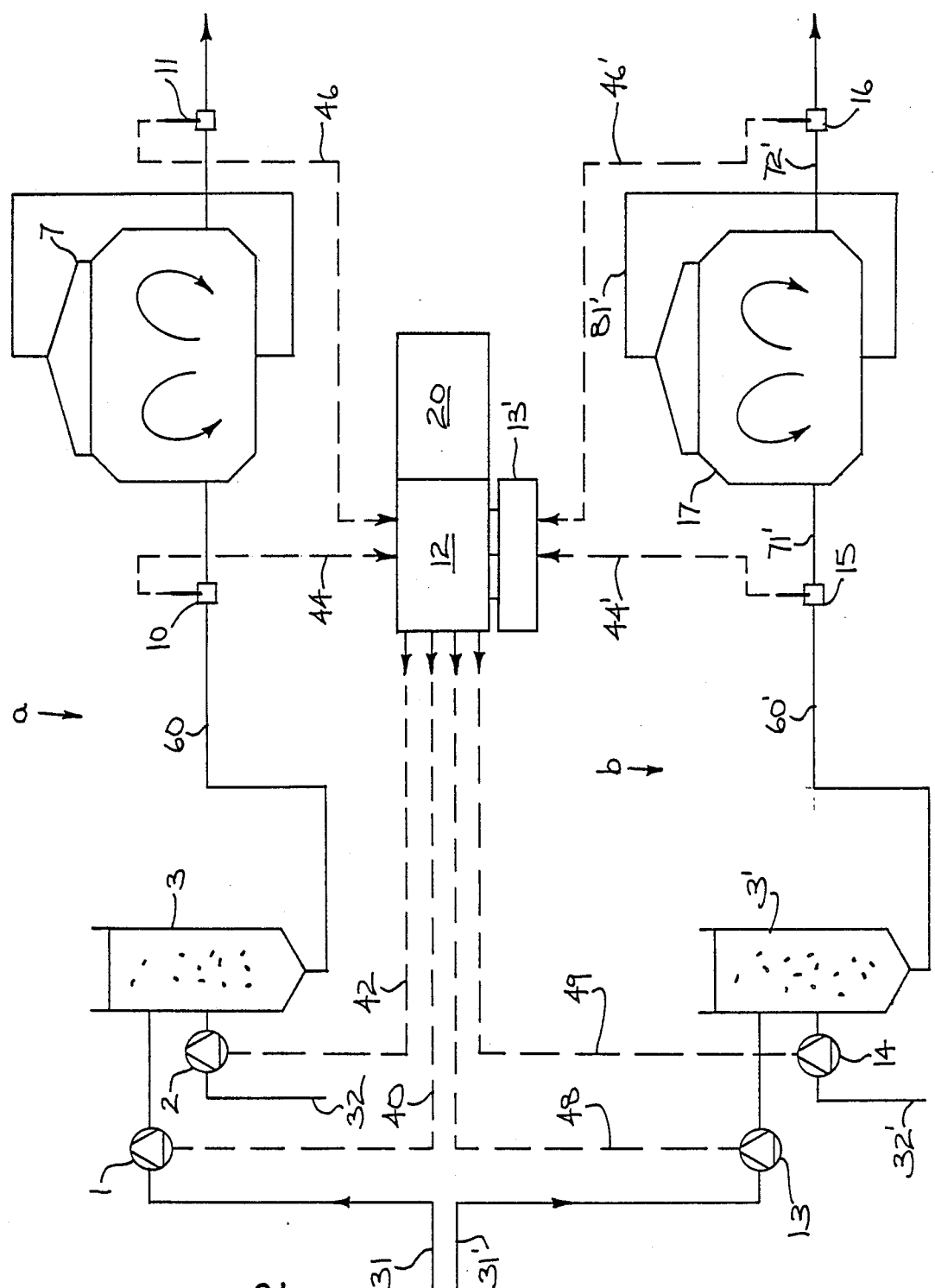
FIG. 2 an apparatus for the simultaneous measurement of BOD and toxicity.

In FIG. 2, the device according to FIG. 1 is once again schematically shown in the upper half and in the lower part a further similar device for toxicity measurement is schematically illustrated. This further device incorporates basically the same apparatus and elements as the previously described device and incorporates thus a further supply conduit 31' to the inlet side of an aeration tank 3' for the supply of polluted liquid. In the supply conduit 31', a further metering pump 13 is arranged. On the upstream side, the supply conduit 31' can be connected with the upstream side of supply conduit 31 so that both conduits 31 and 31' are connected with a not-disclosed vessel containing polluted liquid to be analyzed. On the inlet side of the further aeration vessel 3' is located a feed conduit 32' for diluting water with a metering pump 14. In the discharge conduit 60' from the aeration apparatus 3' a further oxygen electrode 15 is arranged that supplies the oxygen content and the temperature of the liquid stream by means of a control conduit 44' to the process controller 12 through a comparator 13' that records the difference of the measured values of the electrodes connected to the comparator 13'. The oxygen electrode 15 is coupled through a supply conduit 71' with a further reaction vessel 17 similar to the reaction vessel 7 and that is likewise connected in a recirculating circuit 81'. The discharge conduit 72' out of the reaction vessel 17 has a further oxygen electrode 16, that supplies the sensed oxygen content and the temperature of the discharge stream by means of a control conductor 46' to the process controller 12 through the comparator 13'. From the process controller 12 leads a further control conductor 48 to the metering pump 13 for the in-flowing, polluted fluid as well as a control conductor 49 to the metering pump 14 for the dilution water. The process controller 12 acts through the control conductors 48, 49 on the metering pumps 13, 14 in such a way that the concentration of the total fluid supplied to the aeration tank 3' is always the m-fold of the corresponding concentration of the fluid supplied to aeration vessel 3. With the measured values of the oxygen electrodes 15 and 16 in comparison to the measured values that are extracted at the oxygen electrodes 10, 11 an eventual toxic inhibition of the microorganisms can be detected.

The apparatus according to FIG. 2 can also serve as a toxicity meter for the discontinuous measurement with biological standards. In the measurement intervals both apparatus parts are operated with a standardized nutrient solution for the growth and regeneration of the biological standard.

Figure 3:
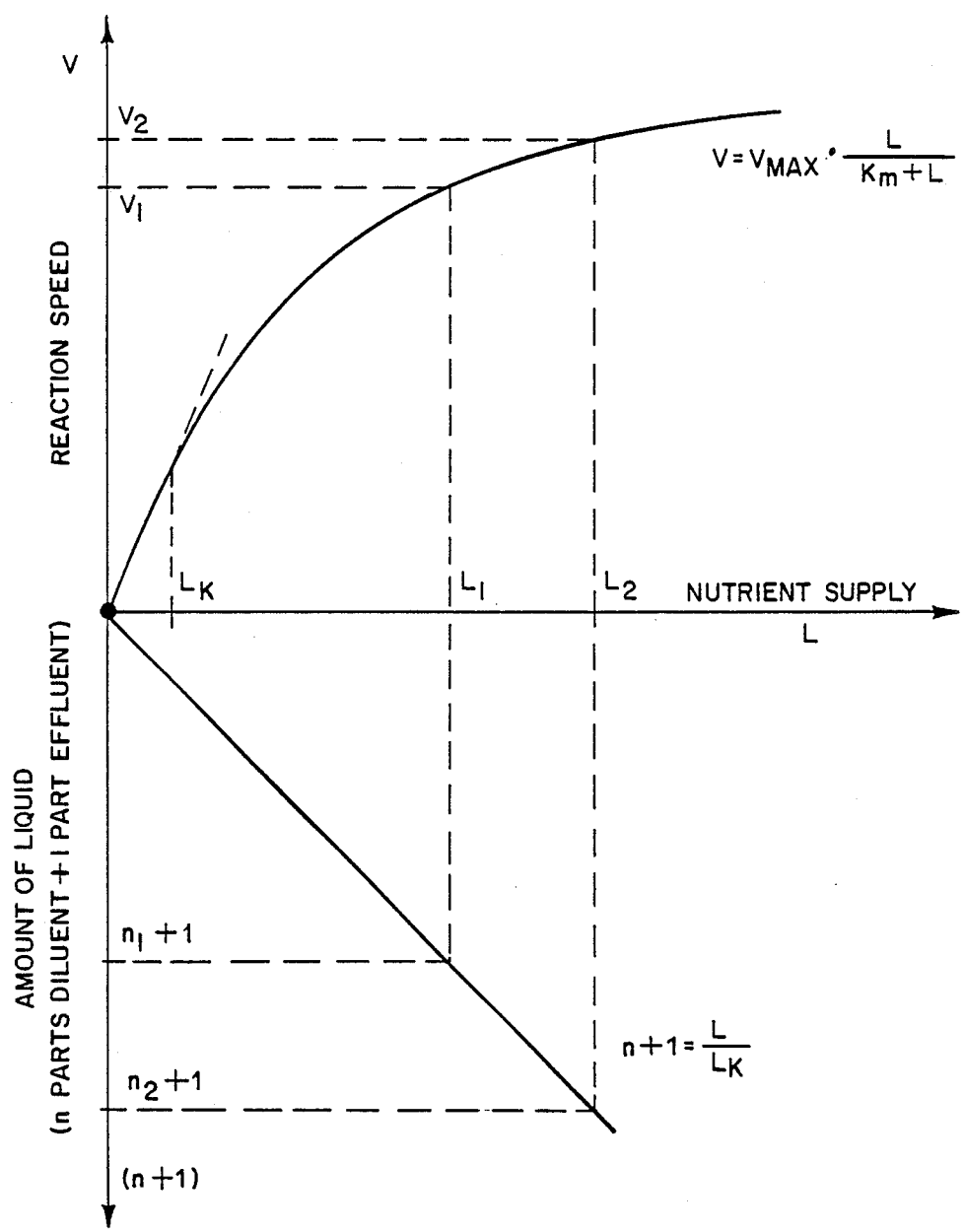
FIG. 3 a reaction diagram.

FIG. 3 shows a reaction diagram. The abscissa is the nutrient supply L. The upper ordinate is reaction speed. The expression of biochemical reaction speed $V_m$ in dependence on nutrient supply L of the effluent defined by equation (1) is graphed in the upper portion of the diagram. Through use of the constant, small nutrient supply $L_k$, the organisms always work in the idealized linear region. The nonlinearities at reaction speeds $V_1$ and $V_2$ with high nutrient supply concentrations L are seen. The lower portion of the graph shows the dilution required to obtain $L_k$ for any given loading L where 1 is a unit of effluent and n is the ratio of diluting water to effluent i.e. the amount of diluting water is n times the amount of effluent. As shown in the lower portion of FIG. 3, the relationship of n+1 to L needed to obtain the constant nutrient supply $L_k$ remains constant.

Figure 4:
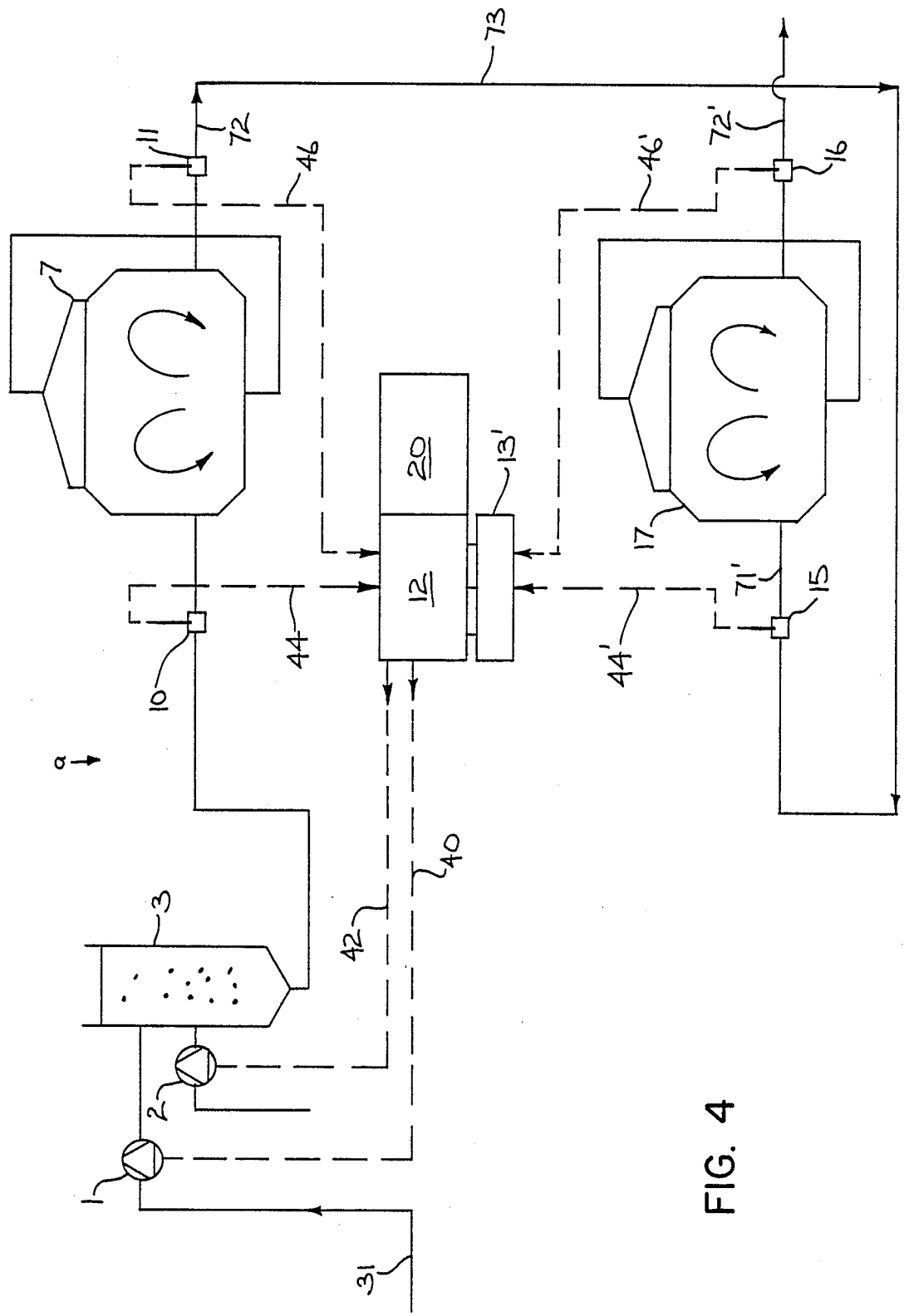
FIG. 4 a schematic diagram of a further exemplary embodiment of the invention.

With the apparatus according to FIG. 4, a transfer conduit 73 is connected in the discharge conductor 72 of the partial stream "a", that is connected with the second oxygen electrode 15. The second oxygen electrode 15 is, in turn, connected through a supply conduit 71' with the second reaction vessel 17 as well as through a control conductor 44' with the comparator 13' of the control. The oxygen electrode 16 inserted in the discharge conduit 72' of the reaction vessel 17 is coupled with the comparator 13' through the control conductor 46'. This series connection of the two reaction vessel 7 and 17 makes possible, besides the BOD measurements, also the determination of the degradableness of the pollution in the partial stream "a". A quantity specified as a BOD value can originate from matter that is easier or harder to degrade. Until now one has, in this circumstance, carried out a calculation that determined the $BOD_5$ value in connection with a COD (chemical oxygen demand). By the process feasible with the device according to FIG. 4, a constant pollution in the part stream "a" is supplied to the microorganism in the first reaction vessel. This pollution is degraded to a residual value in the first reaction vessel, dependent on the composition of the pollutant. This residual pollution in the partial stream flowing in transfer conduit 73 produces, according to its magnitude, differing oxygen differences between oxygen electrodes 15 and 16 with the passage through the second reaction vessel 17. These differing oxygen differences represent a criterium for the evaluation of the degradability of the pollution in the partial stream.

Figure 5:
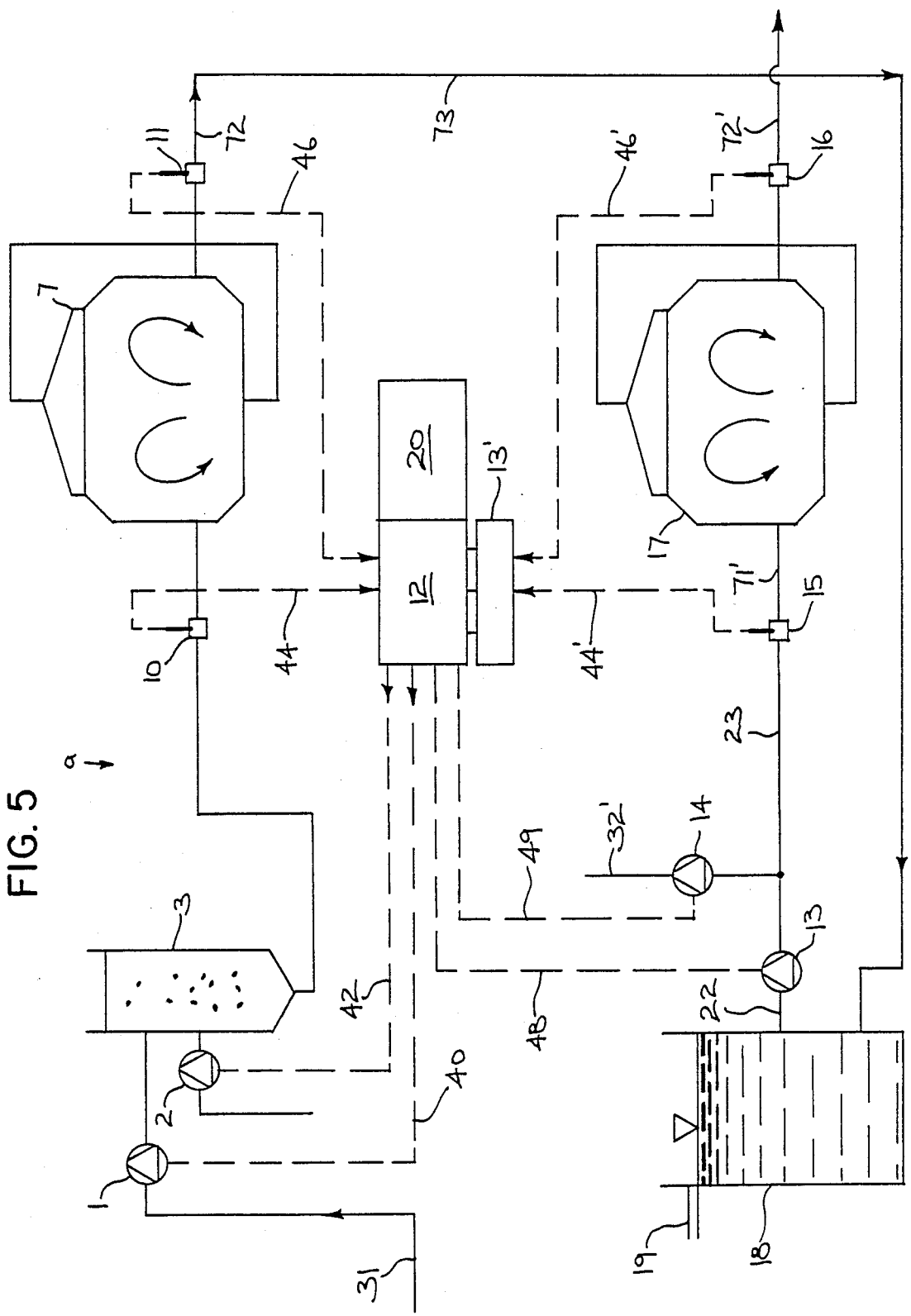
FIG. 5 a schematic diagram of a further exemplary embodiment of the invention.

The device according to FIG. 5 can also be used for the analysis of the level of toxicity, if the conduit 73 opens into a tank 18 in which a drawing off conduit 22 is connected. The drawing off conduit 22 leads through the metering pump 13 to the oxygen electrode 15 and from there through the supply conduit 71' to the second reaction vessel 17. The tank 18 has an overflow 19. In the conduit section 23 between metering pump 13 and oxygen electrode 15, opens the downstream side of the metering pump 14 for the dilution water supplied from the supply conduit 32'. In the conduits, means are provided preventing the return flow of the fluid through the metering pumps 13, 14. If necessary, a further, not disclosed aeration tank may be inserted in the conduit section 23. The control is additionally so employed that the metering pumps 1 and 2 are controlled from the signals of the oxygen electrodes 15 and 16. The metering pump 13 removes fluid from the tank 18 under the regulation from the signal in conductor 48, smaller by a constant factor than that supplied by the metering pump 1. The metering pump 14 is so controlled through conductor 49 that it insures, through a corresponding supplement of dilution water, the necessary constant volume of the flow through the reaction vessel 17. The quantity in the fluid, that is displaced through the overflow 19 in the tank 18 must be supplied through the pump 14 corresponding to the above noted conditions.

If the partial stream "a" flowing through the conduit 73 is diluted by a constant factor, the toxicity of the part stream entering through the supply conduit 71' in the second reaction vessel 17 is reduced corresponding to the dilution so that the activities of the microorganisms in the second reaction vessel 17 are not inhibited or are inhibited to a small extent. This has the result that the difference of the ascertained values from the oxygen electrodes 15 and 16 differs from the difference of the concentrations measured from the oxygen electrodes 10 and 11. From this variation of the differences, the controller 12 determines an existing toxicity of the loading in the partial stream "a". The pumps 13 and 14 so mix the fluid streams that the concentration in the reaction vessel 17 is adjusted lower by a constant factor than that in the reaction vessel 7, whereby the flow volumes in both vessels must be constant and can be similar.

The invention is naturally not limited to the details of the above described exemplary embodiments. Thus, with the device according to FIG. 4, the oxygen electrode 15 can be eliminated so that then the difference of the ascertained oxygen values between the electrodes 11 and 16 are processed by controller 12. Also, a further aeration tank can, if necessary, be connected in series with the second reaction vessel 17.

Preliminary Design

Reaction Time: 5 minutes
Flow volume: 1 liter/min.

From this it follows: At 20° C. and 760 Torr, approximately 9 mg/$O_2$/liter is present so that 9 mg $O_2$/min is available. With higher operating pressure the existing available oxygen can be computed according to Henry's Law $C_s = K_s \cdot P_t$.

The minimum oxygen concentration on the electrode (11) is established at 2 mg $O_2$/liter. The permissible oxygen consumption thus amounts to a maximum of 7mg/liter.

According to the preliminary investigations, there occurs with a specific constant nutrient supply $L_{k,a}$, (corresponding 5 mg $BOD_5$/liter) an oxygen demand of 2.5 g $O_2/m^2 \cdot d = 1.7$ mg $0_2/m^2 \cdot$min and with $L_{k,b}$ (corresponding 25 mg $BOD_5$/liter) an oxygen demand of 5 g $O_2/m^2 d = 3.5$ mg $O_2/m^2$ min.

Under these assumptions an oxygen supply of 7 mg/min in consumed through the use of 4.1 to 2.05 $m^2$ growing surfaces on the bodies 9.

For the bodies are selected: hollow cylinders, inner diameter 3 mm, height 3 mm with a specific outer surface of 2.1 $m^2$/liter with most porous packing. This is 37,037 pieces/liter.

With the corresponding calculation the reaction vessel (7) is filled with 72,310 hollow cylinders (4.1 $m^2$) and the reaction vessel (17) filled with 36,155 hollow cylinders (2.5 $m^2$)

The hollow cylinders take up, with the loosest arrangement, 39 to 19.5% of the reaction volume. There thus exists for them sufficient movement possibilities.

Corresponding to the preliminary design $L_{k,a}$ is determined at 5 mg BOD$_5$/liter and $L_{k,b}$ with 25 mg BOD$_5$/liter.

With a mixture ratio 1:n, the total nutrient supply L - measured as BOD$_5$/liter—is calculated as follows:

$$BOD_a = L_{k,a} \cdot (n + 1) = L \text{ (mg BOD}_5\text{/liter)}$$

$$BOD_b = L_{k,b} \cdot \frac{(n + 1)}{m} \cdot \frac{\Delta O_{2b}}{\Delta O_{2b,T}} \text{ (mg BOD}_5\text{/liter)}$$

The controller processes the value $L_k$ not as a constant but rather increases or decreases the values $L_{k,a}$ and $L_{k,b}$ about 1.4% for each 0.1 O$_2$ mg/liter deviation from the desired value $\Delta O_2$ between electrodes (10) and (11).

In the calculation the following abbreviations means:
L=nutrient material concentration
BOD=biological oxygen demand
BOD$_5$=biological oxygen demand in five days
$L_k$=constant nutrient supply (measured as BOD$_5$ mg/liter)
a,b=indexes for the reaction behaviors in the vessels (7) and (17)
$\Delta O_2$=calibrating value, that on the basis of the effluent water fluctuation to be expected (clarifier supply or discharge) is adjusted through variations of the growing surfaces.
$\Delta O_{2b,T}$=a control value that is compared with the calibration value $\Delta O_{2b}$
m=a factor for the variation of the nutrient material concentration in container (17).
n=the dilution factor of dilution water to effluent, taken with respect to a constant amount of effluent, for example, 1 part effluent to "n" parts dilution water
$L_{(t)}$=a nutrient material concentration at the time point "t"

The functional description of the measuring device with the aid of a computation example begins with the description of a stationary analysis condition (dilution ratio, effluent/dilution water 1:n$_1$).

A constant nutrient amount $L_{k,a}$ (in the example 5 mg BOD$_5$/liter) is supplied to the organisms in the reaction vessel (7). The mixture ratio amounts to 1:n$_1$ and the $BOD_a = L_{k,a} \cdot (n_1 + 1) = L$. The oxygen difference between the electrodes (10) and (11) totals $\Delta O_{2a}$ (in the example 7 mg O$_2$/liter).

With an increase in the pollutant concentration L, the organisms react with the increased respiratory activity. Through the increased respiratory activity, the electrodes (10) and (11) register a greater oxygen difference. With $\Delta O_{2a}$=7.1 mg O$_2$/liter the pumps are so controlled that the contaminated water portion (pump 1) decreases and the dilution water portion (pump 2) is increased until the O$_2$ difference between electrodes (10) and (11) again is adjusted to 7 mg O$_2$/liter.

The new mixture ratio amounts then 1:n$_2$ and the new $BOD_a = L_{k,a} \cdot (n_2 + 1) = L$.

With the decrease of the pollution concentration L, the process runs in the opposite direction.

With the parallel operation of two reaction vessels for the BOD measurement with simultaneous toxicity monitoring, the pumps (1) (13) and (2) (14) are controlled in the previously described manner through the electrodes (10) and (11). The pump (13) supplies however m-fold the volume of the pump (1).

The electrodes (15) and (16) monitor only the oxygen consumption in the reaction vessel (17). If the O$_2$ difference $\Delta O_{2b,T}$ corresponds to the preliminary calculation value $\Delta O_{2b}$ (in the example 7 mg O$_2$/liter) then there exists no oxygen consumption inhibition. In this case BOD$_a$ and BOD$_b$ are similar.

With toxicity effects present, the ratio BOD$_a$/BOD$_b$ gives, in connection with the dilution amount 1:n, data about the level of existing oxygen consumption inhibition.

We claim:

1. Apparatus for measuring the degree of pollution of an aqueous liquid resulting from biodegradable components contained in the aqueous liquid, said apparatus comprising:
    first means for providing a sample stream of the aqueous liquid;
    second means for providing biologically neutral water to the sample stream to provide a diluted sample stream;
    means for obtaining oxygenation of the diluted sample stream to provide an oxygenated, diluted sample stream;
    a reaction vessel having an inlet and an outlet, said inlet receiving the oxygenated, diluted sample stream, said reaction vessel containing a biological bath having an essentially constant microbiological living mass for which the biodegradable components of the aqueous liquid act as nutrients and in which oxygen is consumed in biodegrading the biodegradable components;
    means for determining the oxygen consumption in said reaction vessel and means coupled to said first and second means for regulating, via said first and second means, the amount of dilution of the sample stream to maintain essentially constant oxygen consumption in said reaction vessel while providing a constant volumetric flow rate of the oxygenated diluted sample stream through the reaction vessel; and
    means for indicating the degree of pollution of the aqueous liquid in accordance with the amount of dilution of the sample stream.

2. The apparatus according to claim 1 wherein said oxygen consumption determining means includes an oxygen sensor at the outlet of said reaction vessel.

3. The apparatus according to claim 2 wherein said oxygen consumption determining means includes an oxygen sensor at the inlet of said reaction vessel.

4. The apparatus according to claim 3 wherein said oxygen consumption determining means includes comparator means coupled to said oxygen sensors and to said regulating means.

5. The apparatus according to claim 1 wherein said first and second means comprise metering pumps.

6. The apparatus according to claim 1 wherein said oxygenating means comprises an aeration tank receiving the diluted sample stream.

7. The apparatus according to claim 1 wherein said reaction vessel contains a plurality of free floating bodies with growing surfaces for said living mass.

8. The apparatus according to claim 7 wherein said reaction vessel has means for maintaining said free floating bodies in turbulent movement.

9. The apparatus according to claim 8 wherein said turbulent movement maintaining means includes a recirculating conduit through which the contents of said vessel are continuously circulated.

10. The apparatus according to claim 7 wherein said free floating bodies are so formed as to possess growing surfaces protected against mechanical influences.

11. The apparatus according to claim 10 wherein said free floating bodies are formed as hollow cylinders.

12. The apparatus according to claim 1 further including means for providing a buffer solution to the sample stream.

13. The apparatus according to claim 1 further including means for pressurizing said reaction vessel.

14. The apparatus according to claim 1 further defined as apparatus for determining toxicity present in the aqueous liquid, said apparatus further including:
third means for providing an additional sample stream of the aqueous liquid;
fourth means for providing biologically neutral water to said additional sample stream to provide a diluted additional sample stream;
means for obtaining oxygenation of the diluted additional sample stream to provide an oxygenated, diluted additional sample stream;
an additional reaction vessel having an inlet and an outlet, said inlet receiving the oxygenated, diluted additional sample stream, said additional reaction vessel containing a biological bath having an essentially constant microbiological living mass for which the biodegradable components of the aqueous liquid act as nutrients and in which oxygen is consumed in biodegrading the biodegradable components;
said regulating means also being coupled to said third and fourth means for diluting, via said third and fourth means, the additional sample stream lower by a constant factor than that of the sample stream while providing a constant volumetric flow rate of the oxygenated, diluted additional sample stream through the additional reacion vessel, and wherein said oxygen consumption determining means is also for determining the oxygen consumption in said additional reaction vessel;
means for comparing the oxygen consumption in said reaction vessel and in said additional reaction vessel; and wherein said indicating means is also for indicating the toxicity present in the aqueous liquid in accordance with said comparison.

15. The apparatus according to claim 14 wherein said oxygen consumption determining means includes an oxygen sensor at the outlet of said additional reaction vessel.

16. The apparatus according to claim 15 wherein said oxygen consumption determining means includes an oxygen sensor at the inlet of said additional reaction vessel.

17. The apparatus according to claim 14 wherein said third and fourth means comprise metering pumps.

18. The apparatus according to claim 14 wherein said means for obtaining oxygenation of the additional diluted sample stream comprises an aeration tank receiving the diluted additional sample stream.

19. The apparatus according to claim 14 wherein said additional reaction vessel contains a plurality of free floating bodies with growing surfaces for said living mass in said additional reaction vessel.

20. The apparatus according to claim 19 wherein said additional reaction vessel has means for maintaining said free floating bodies in turbulent movement in said additional reaction vessel.

21. The apparatus according to claim 20 wherein said turbulent movement maintaining means includes a recirculating conduit through which the contents of said additional reaction vessel are continuously circulated.

22. The apparatus according to claim 19 wherein said free floating bodies in said additional reaction vessel are so formed as to possess growing surfaces protected against mechanical influences.

23. The apparatus according to claim 22 wherein said free floating bodies are formed as hollow cylinders.

24. The apparatus according to claim 14 further including means for providing buffer solution to the diluted additional sample stream.

25. The apparatus according to claim 14 further including means for pressurizing said additional reaction vessel.

26. The apparatus according to claim 1 further defined as apparatus for determining the degradability of the biodegradable components in the aqueous liquid, said apparatus including;
an additional reaction vessel having an inlet and an outlet, said inlet receiving the sample stream discharged at the outlet of said reaction vessel, said additional reaction vessel containing a biological bath having a microbiological living mass for which biodegradable components of the sample stream discharged from said reaction vessel act as nutrients and in which oxygen is consumed in biodegrading such components;
wherein said oxygen consumption determining means is also for determining the oxygen consumption in said additional reaction vessel; and
means for comparing the oxygen consumption in said reaction vessel and in said additional reaction vessel;
and wherein indicating means is also for indicating the degradability of the biodegradable components in accordance with said comparison.

27. The apparatus according to claim 26 wherein said oxygen consumption determining means includes an oxygen sensor at the inlet and at the outlet of said additional reaction vessel.

28. The apparatus according to claim 26 wherein said additional reaction vessel contains a plurality of free floating bodies with growing surfaces for said living mass in said additional reaction vessel.

29. The apparatus according to claim 28 wherein said additional reaction vessel has means for maintaining said free floating bodies in turbulent movement.

30. The apparatus according to claim 29 wherein said turbulent movement maintaining means includes a recirculating conduit through which the contents of said vessel are continuously circulated.

31. The apparatus according to claim 28 wherein said free floating bodies are so formed as to possess growing surfaces protected against mechanical influences.

32. The apparatus according to claim 31 wherein said free floating bodies are formed as hollow cylinders.

33. The apparatus according to claim 26 further including means for pressurizing said additional reaction vessel.

34. Apparatus for determining toxicity present in an aqueous liquid, the aqueous liquid containing biodegradable components, said apparatus comprising:
first means for providing a sample stream of the aqueous liquid;

second means for providing biologically neutral water to the sample stream to provide an initially diluted sample stream;

means for obtaining oxygenation of the initially diluted sample stream to provide an oxygenated, initially diluted sample stream;

a first reaction vessel having an inlet and an outlet, said inlet receiving the oxygenated, initially diluted, sample stream, said first reaction vessel containing a first biological bath having a microbiological living mass for which the biodegradable components of the aqueous liquid act as nutrients and in which oxygen is consumed in biodegrading the biodegradable components;

first oxygen consumption determining means for determining the oxygen consumption in said first reaction vessel;

third means for providing biologically neutral water to sample stream emerging from said outlet of said first reaction vessel to provide a further diluted sample stream which is diluted by a factor such that a relationship between the initial dilution and the further dilution remains constant;

a second reaction vessel having an inlet and an outlet, said second reaction vessel containing a second biological bath having an essentially constant microbiological living mass for which biodegradable components of the further diluted sample stream act as nutrients and in which oxygen is consumed in biodegrading such biodegradable components;

second oxygen consumption determining means for determining the oxygen consumption in said second reaction vessel;

means coupled to said first, second, and third means for regulating, via said first, second, and third means, the amount of the initial dilution of the sample stream in accordance with the oxygen consumption determination from said second reaction vessel to maintain essentially constant oxygen consumption in said second reaction vessel while providing a constant volumetric flow rate of the oxygenated, initially diluted sample stream through the first reacion vessel and a constant volumetric flow rate of the further diluted sample stream through the second reaction vessel; and means for comparing the oxygen consumption determination from said first reaction vessel with the determination from said second reaction vessel and means for indicating the toxicity present in the aqueous liquid employing the results of the comparison.

35. The apparatus according to claim 34 wherein said first and second oxygen consumption determining means comprise oxygen sensors at the inlets and outlets of said reaction vessels.

36. The apparatus according to claim 34 wherein said first, second, and third means comprise metering pumps.

37. The apparatus according to claim 34 wherein said oxygenating means comprises an aeration tank receiving the initially diluted sample stream.

38. The apparatus according to claim 34 wherein said reaction vessels each contain a plurality of free floating bodies with growing surfaces for said living masses.

39. The apparatus according to claim 38 wherein said reaction vessels have means for maintaining said free floating bodies in turbulent movement.

40. The apparatus according to claim 38 wherein said free floating bodies are so formed as to possess growing surfaces protected against mechanical influences.

41. The apparatus according to claim 34 further including means for providing a buffer solution to said sample stream.

42. The apparatus according to claim 34 further including means for pressurizing said reaction vessels.

* * * * *